United States Patent
Tanaka et al.

(12)

(10) Patent No.: US 6,482,640 B1
(45) Date of Patent: Nov. 19, 2002

(54) HYBRIDIZATION DEVICE, CASE, SUPPORT, AND LABEL AGENT

(75) Inventors: Toshiaki Tanaka, Kanagawa (JP); Kenji Yamamoto, Kanagawa (JP); Koichiro Hatano, Kanagawa (JP); Katsuya Mizuno, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 09/889,990

(22) PCT Filed: Nov. 15, 2000

(86) PCT No.: PCT/JP00/08049

§ 371 (c)(1), (2), (4) Date: Dec. 31, 2001

(87) PCT Pub. No.: WO01/38482

PCT Pub. Date: May 31, 2001

(30) Foreign Application Priority Data

Nov. 25, 1999 (JP) ............................................. 11-334120

(51) Int. Cl.[7] ................................................. C12M 1/34
(52) U.S. Cl. ................................ 435/287.2; 435/288.3; 435/288.5
(58) Field of Search ...................... 435/6, 285.1, 287.1, 435/287.2, 288.5, 288.3; 204/400, 403

(56) References Cited

U.S. PATENT DOCUMENTS 6,066,448 A * 5/2000 Wohlstadter et al. ........ 204/400
6,342,359 B1 * 1/2002 Lee et al. ................. 435/285.1

FOREIGN PATENT DOCUMENTS

| JP | 08-154656 | 6/1996 |
| JP | 10-146183 | 2/1997 |
| JP | 10-239240 | 9/1998 |
| WO | WO 93/10267 | 5/1993 |

* cited by examiner

Primary Examiner—David A. Redding
(74) Attorney, Agent, or Firm—Pillsbury Winthrop LLP

(57) ABSTRACT

The present invention provides a hybridization device, case, support and labeling reagent which can enhance the efficiency of the hybridization reaction, save more time for the reaction and improve the detection sensitivity.

A case (1) comprises: a metal support (2) made of platinum-covered titanium and having probe DNA immobilized thereon; counter electrodes (2a) and (2b) for applying a voltage between the metal support (2); a cap (3); and a filler port (23).

As a result, a hybridization reaction can be performed in an efficient manner in a short time. In addition an electrogenerated chemiluminescent substance may be used for detection.

7 Claims, 6 Drawing Sheets

HYBRIDIZATION DEVICE, CASE, SUPPORT, AND LABEL AGENT

FIELD OF THE INVENTION

The present invention relates to a hybridization device, a case for performing a hybridization reaction in the device, a support for performing a hybridization reaction in the case, and a labeling reagent for labeling a biological substance used for the hybridization.

BACKGROUND ART

Conventionally, a hybridization reaction include steps of: immobilizing probes on an insulating glass plate as a support; dropping a hybridization reaction solution containing a fluorescence-labeled sample on the support; covering the support with a glass cover; and leaving the support in a thermostat for a predetermined period of time. Thereafter, the support is taken out from the thermostat, and washed with a washing solution. The fluorescent substance as the label is excited and the resulting fluorescence is read with a detector, thereby identifying the sample hybridizing to the probes. The above-mentioned probes and sample are all biological substances, specifically DNA or RNA. Hybridization may take place between DNA and RNA. Alternatively, samples may be immobilized on a support to be subjected to hybridization with a hybridization reaction solution containing a fluorescence-labeled probe. Herein, a hybridization reaction between DNA probes immobilized on a support and labeled DNA are described as an example. However, the present invention is not limited thereto.

When a hybridization reaction is carried out as described above, the reaction takes 6 to 7 hours, requiring long time. Thus, in general, multiple expensive hybridization devices are used in line to perform multiple hybridization reactions at the same time, which requires a large installation space.

The present invention has an objective of providing a hybridization device, case, support and labeling reagent, which can enhance the efficiency of a hybridization reaction, save more time for the reaction and improve the detection sensitivity.

DISCLOSURE OF THE INVENTION

A support of the present invention comprises a metal for supplying a charge to a hybridization reaction solution. Accordingly, a charge can be supplied to the reaction solution to attract a biological substance contained in the hybridization reaction solution to the support side. Moreover, an electrogenerated chemiluminescent substance may be used as a labeling reagent.

By immobilizing a biological substance on the support, the support may, for example, be used directly for diagnosis of a specific disease.

A case of the present invention comprises an electrode for supplying a charge to a hybridization reaction solution.

By storing the above-described support, the case may, for example, be used directly for diagnosis of a specific disease as described above.

A hybridization device of the present invention supplies electricity to a case used for a hybridization reaction to supply a charge to a hybridization reaction solution.

A labeling reagent of the present invention comprises an electrogenerated chemiluminescent substance for labeling a biological substance.

BEST MODES FOR CARRYING OUT THE INVENTION

Hereinafter, a preferred embodiment of the present invention will be described in detail with reference to the accompanying drawings.

Figure 1:
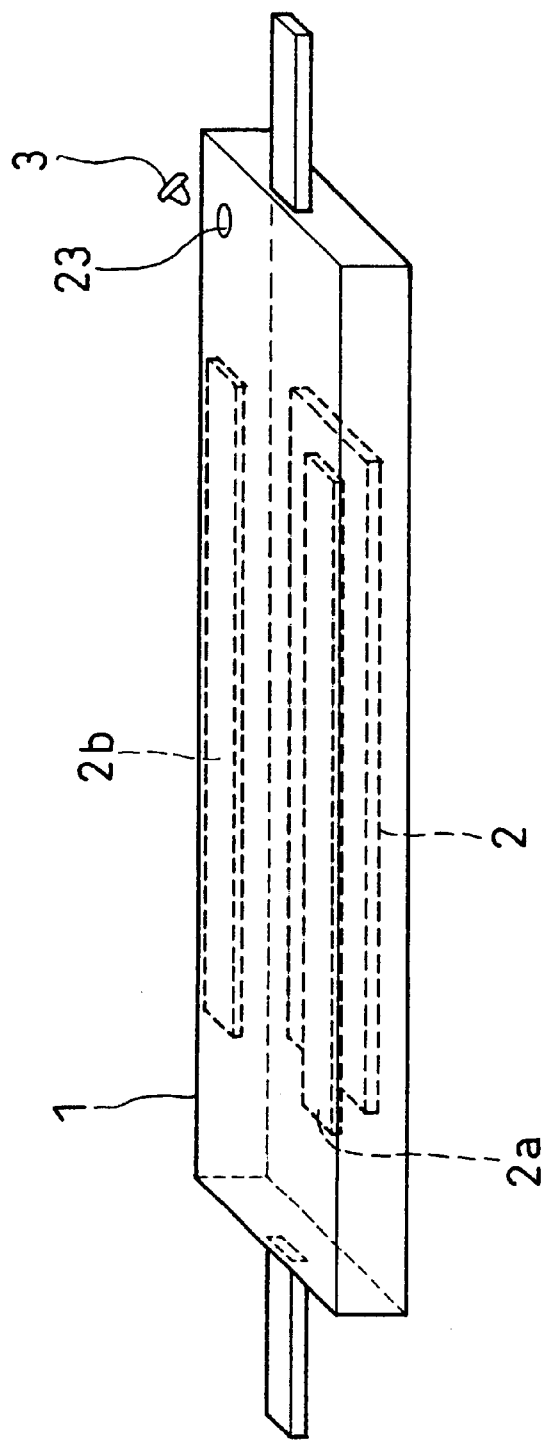
FIG. 1 is a perspective view showing a structure of a case used for a hybridization reaction according to one embodiment of the present invention.

FIG. 1 is a perspective view showing a structure of a case used for a hybridization reaction according to one embodiment of the invention.

The case 1 is provided with a metal support 2, counter electrodes 2a and 2b, a cap 3 and a filler port 23.

Preferably, the case 1 is transparent for optically detecting the results of the reactions and is made of an acrylic resin to be resistant against chemicals. The metal support 2 is firmly attached to the center of the inner bottom of the case 1. The counter electrodes 2a and 2b are firmly attached to the case 1 above the both sides of the metal support 2 so that the counter electrodes 2a and 2b do not interfere with observation from above.

The metal support 2 has a size of, for example, $25 \times 75 \times 2$ $mm^3$ and is immobilized with probe DNA. Accordingly, the surface of the metal support 2 has to be uniform and needs to be stable as an electrode. Therefore, in this embodiment, platinum-covered titanium is used.

Since the counter electrodes 2a and 2b are not transparent in this case, they have to be placed such that they do not interfere with the detection with a cooled CCD. If a transparent electrode is used in place of the counter electrodes 2a and 2b, a single electrode as large as the metal support 2 may be provided above the metal support 2.

Figure 2:
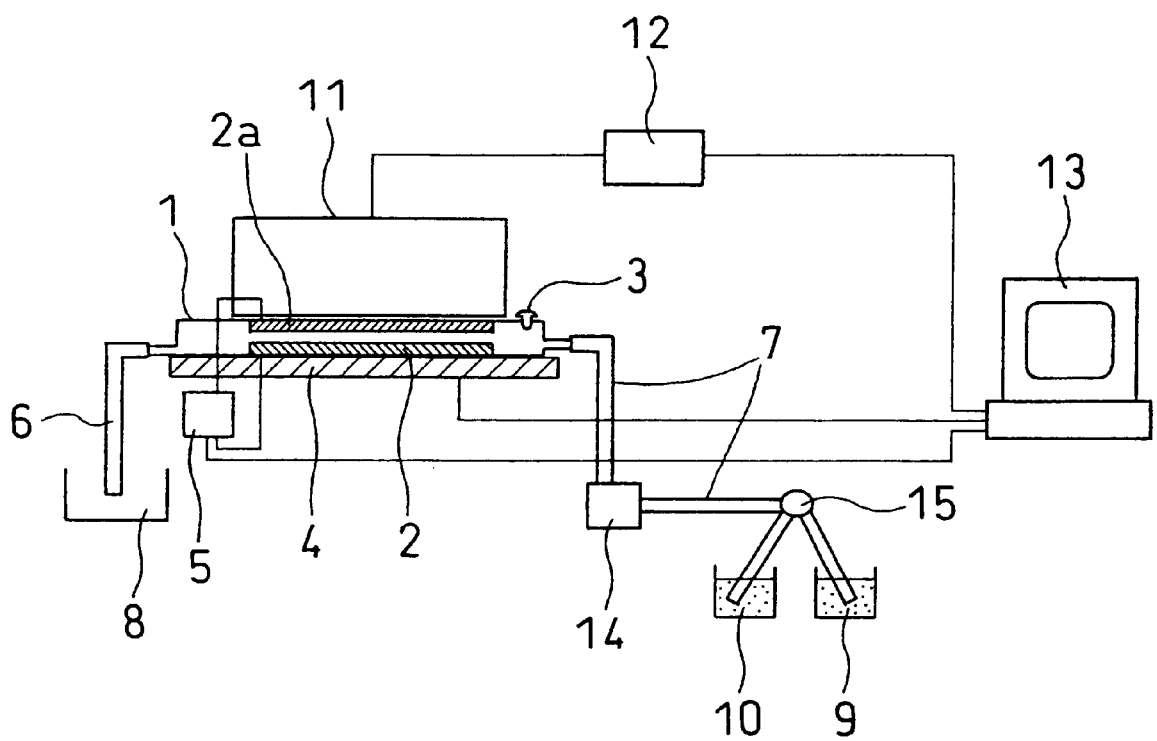
FIG. 2 is a schematic view showing a structure of a hybridization device according to one embodiment of the present invention.

FIG. 2 is a schematic view showing a hybridization device according to the embodiment of the invention. The case 1 is mounted with the metal support 2, injected with a hybridization reaction solution, and is sealed with the cap 3. The case 1 is then placed on and heated by a Peltier element 4. The Peltier element 4 is connected to a computer 13 so that the reaction temperature can be controlled. The metal support 2 is charged positive by a power switch 5 and a voltage is applied between the metal support 2 and the respective counter electrodes 2a and 2b, thereby applying an electric field to the reaction hybridization solution for a hybridization reaction. The power switch 5 is connected to and controlled by the computer 13. The voltage applied for this hybridization reaction is about 100 V. After the reaction, the hybridization reaction solution is discharged from the case 1 to a discharged solution reservoir 8 via a discharging tube 6. By doing so, un-reacted sample DNA 16 (see FIG. 3) is discharged along with the hybridization reaction solution. Thereafter, a washing solution in a washing solution reservoir 9 is injected into the case 1 via an injection tube 7 by the pump 14, and similarly discharged into the discharged solution reservoir 8. According to the present embodiment, 0.2×SSC/0.1% SDS solution is used as the washing solution. Furthermore, a TPA (Tripropylamine) solution in a TPA solution reservoir 10, which is necessary for the later-described electrogenerated chemiluminescence is injected into the case 1. The solution to be injected is selected with a switch 15. After injecting the TPA solution, the power switch 5 is turned on again to apply a voltage to the metal support 2 for electrogenerated chemiluminescence. The current for the electrogenerated chemiluminescence is about 100 µA. However, since this current is required for oxidizing later-described $Ru^{2+}$ to obtain $Ru^{3+}$, an optimal luminescence intensity is adjusted at about 50 to 150 µA (variable). The luminescence is detected by the cooled CCD 11 on the case 1. After the detection, the TPA solution in the case 1 is discharged. The detected data is sent to the computer 13 via an A/D converter 12.

Figure 3:
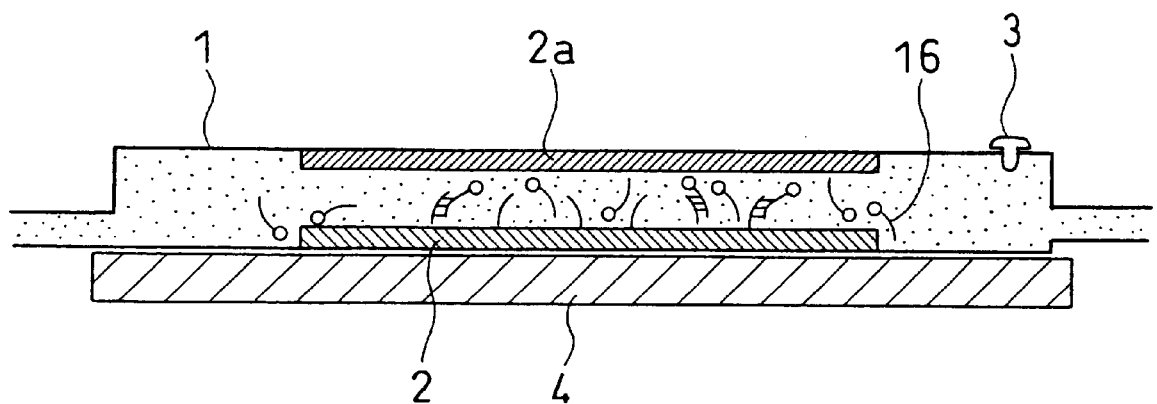
FIG. 3 is a schematic view for illustrating the hybridization reaction according to one embodiment of the present invention.

FIG. 3 is a schematic view for illustrating the hybridization reaction according to the embodiment of the present invention. The power switch 5 is turned on to apply a voltage so that the negatively-charged sample DNA 16 in the case 1 is attracted to the positively-charged metal support 2, thereby increasing the chance of the reaction and thus improving the reaction efficiency of the reaction with the probe DNA on the metal support 2. As a result, time required for the hybridization reaction can be saved.

During the reaction, the case 1 is heated from beneath by the Peltier element 4 to maintain a constant reaction temperature.

Figure 4:
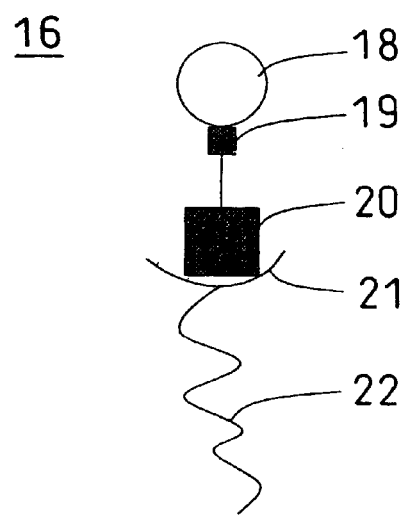
FIG. 4 is a schematic view for illustrating a structure of sample DNA introduced with a ruthenium complex according to one embodiment of the present invention.

FIG. 4 is a schematic view for illustrating a structure of the sample DNA 16 introduced with a ruthenium complex 18. The sample DNA 16 in the hybridization reaction solution is modified with an electrogenerated chemiluminescent substance. The present device employs the ruthenium complex 18 as a luminescent substance and Tripropylamine (TPA) 17 as an electron donor, thereby enabling detection based on electrogenerated chemiluminescence. According to the present embodiment, N-hydroxysuccinimide-activated ester (NHS ester) 19 is used as a cross-linking agent. The NHA ester 19 is bound to streptoavidin 20. On the other hand, sample DNA 22 is biotinylated with biotin 21. Through this streptoavidin-biotin binding, the ruthenium complex 18 can be bound to the sample DNA 22. The sample DNA 22 may be biotinylated by using a biotinylation kit commercially available from Pierce or else.

Figure 5:
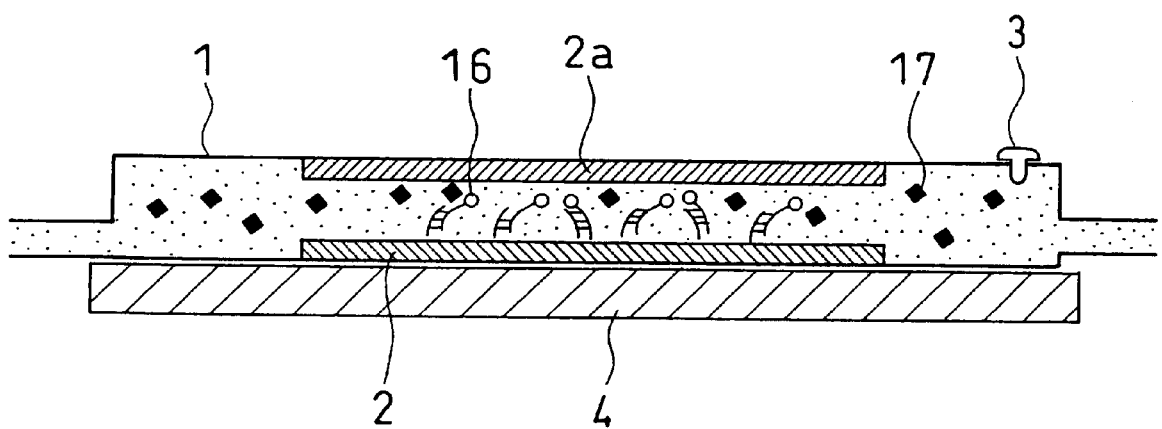
FIG. 5 is a schematic view showing electrogenerated chemiluminescence according to one embodiment of the present invention.

FIG. 5 is a schematic view for illustrating electrogenerated chemiluminescence according to the embodiment of the present invention. The ruthenium complex 18 modifying the sample DNA 22 reacts with the TPA 17 upon application of the voltage to the metal support 2, and results luminescence.

Figure 6:
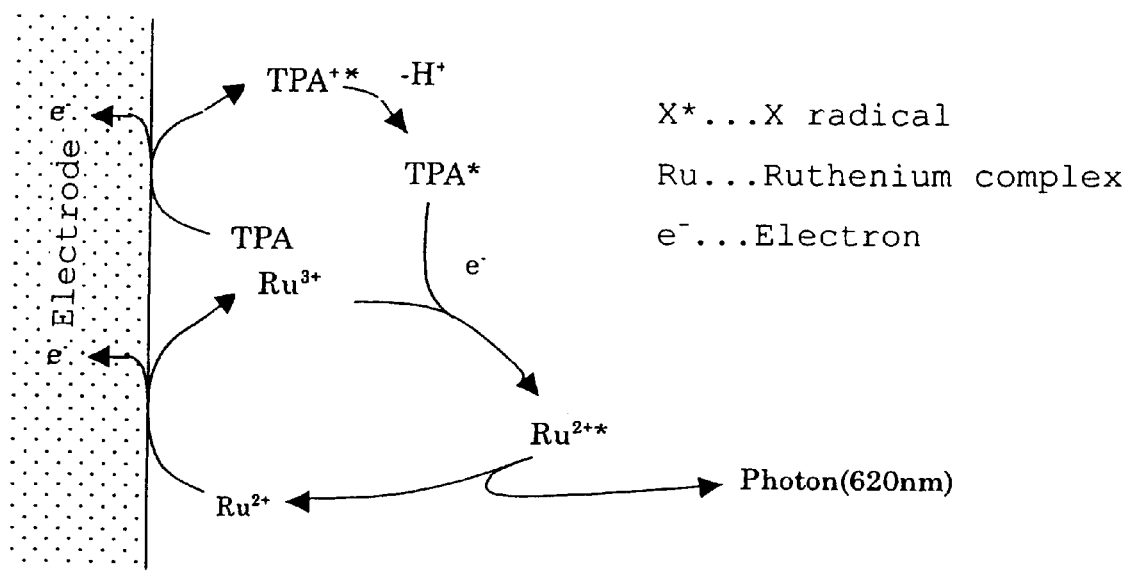
FIG. 6 is a diagram (part 1) for illustrating a reaction between the ruthenium complex and TPA on a metal support.
Figure 7:
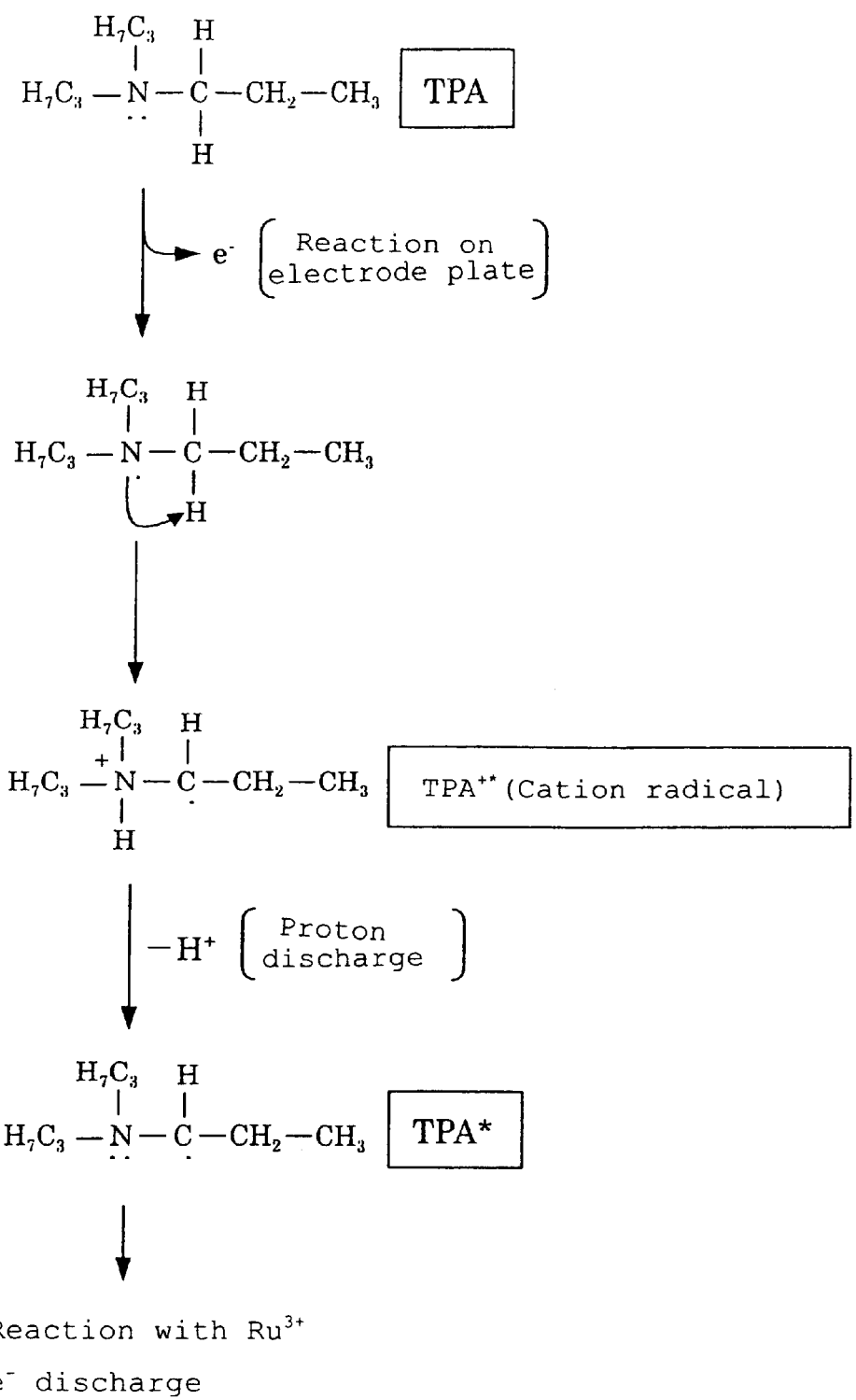
FIG. 7 is a diagram (part 2) for illustrating the reaction between the ruthenium complex and the TPA on the metal support.

FIGS. 6 and 7 are diagrams for illustrating the reaction between the ruthenium complex 18 and the TPA 17 on the metal support 2. First, the TPA 17 discharges an electron on the electrode plate and becomes a cation radical (TPA+*). Since the cation radical is very unstable, it discharges a proton (H+) to be a radical, but because it is still unstable, it further discharges an electron through a reaction with $Ru^{3+}$. On the other hand $Ru^{2+}$ discharges an electron on the electrode plate to become $Ru^{3+}$ and receive an electron through the reaction with the TPA radial (TPA*), but because it is still unstable (excitation state, $Ru^{2+*}$), it discharges a photon and returns to stable $Ru^{2+}$.

The present invention is not limited to the above-described embodiment.

The metal support may be, other than the platinum-covered titanium, a platinum plate, a stainless plate, a titanium/platinum clad or the like. The titanium/platinum clad is obtained by mounting a thin platinum plate on a thin titanium plate with bolts. Since the platinum-covered titanium is obtained by plating a titanium substrate with platinum, a rough surface in a molecular level can be obtained as a general outcome of plating. Thus, the platinum-covered titanium is more efficient as an electrode compared to the above-mentioned platinum plate, the stainless plate or the titanium/platinum clad. The metal support is a good electric conductor owing to the metal and thus, for example, an insulating substrate such as a glass substrate covered with a metal can be used. The metal is not necessarily exposed on the surface, and the metal surface may be covered with a thin dielectric substance for protecting the metal from the solution, as long as the support functions as a good electric conductor such that a charge can be supplied from the metal support to the solution and that the ruthenium complex can react with the TPA.

INDUSTRIAL APPLICABILITY

As described above, according to the present invention, a hybridization reaction can be performed in an efficient manner in a short time. By using an electrogenerated chemiluminescent substance for detection, the detection can be repeatedly be performed. By adjusting the amount and time of the charge supplied from the electrode, an appropriate luminescent intensity can be obtained for each sample.

What is claimed is:

1. A case for hybridization reaction, wherein the case is sealed by a cap and provided with an inlet for injecting a hybridization solution into the case, the case further comprising a metal support and an electrode which are disposed opposite each other on respective internal surfaces of the case.

2. A case for hybridization reaction according to claim 1, wherein a probe is immobilized on the metal support, and a hybridization solution containing a sample is injected into the case via the inlet.

3. A case for hybridization reaction according to claim 1, wherein the case is adapted such that a discharge tube and an injection tube can be connected thereto, so that a solution in the case can be discharged via the discharge tube and a solution can be injected into the case via the injection tube.

4. A case for hybridization reaction according to claim 2, wherein the case is adapted such that a discharge tube and an injection tube can be connected thereto, so that a solution in the case can be discharged via the discharge tube and a solution can be injected into the case via the injection tube.

5. A case for hybridization reaction according to one of claims 1–4, wherein the case is transparent and can be directly heated when placed on a heater.

6. A case for hybridization reaction according to claim 4, wherein the case is connected between the discharge tube which is communicated with a liquid waste reservoir and the injection tube which is communicated, via a pump, to a washing solution reservoir or a tripropylamine solution reservoir selectively by a switch, wherein the metal support and electrodes oppositely disposed on the respective internal surfaces of the case are connected to a power switch for applying voltage between the support and the electrodes, and wherein after a hybridization reaction is caused, by the application of voltage between the metal support and the electrodes by the power switch, between the probe immobilized on the metal support and the sample contained in the hybridization solution injected via the inlet, the washing solution in the washing solution reservoir is injected into the case and the hybridization solution in the case is discharged to the liquid waste reservoir by the operation of the pump and the switch, and, following the washing solution, a tripropylamine solution in a tripropylamine solution reservoir is injected into the case by the operation of the pump and the switch.

7. A case for hybridization reaction according to claim 5, wherein the case is connected between the discharge tube which is communicated with a liquid waste reservoir and the injection tube which is communicated, via the pump, with a washing solution reservoir or a tripropylamine solution reservoir selectively by a switch, and is placed on a heater, wherein the metal support and the electrodes oppositely disposed on the respective internal surfaces of the case are connected to the power switch for applying voltage therebetween, wherein after a hybridization reaction is caused, by the application of voltage between the metal support and the electrodes by the power switch and by the operation of the heater, between the probe immobilized on the metal support and the sample contained in the hybridization solution injected via the inlet, the washing solution in the washing solution reservoir is injected into the case and the hybridization solution in the case is discharged to the liquid waste reservoir by the operation of the pump and the switch, and, following the washing solution, a tripropylamine solution in a tripropylamine solution reservoir is injected into the case by the operation of the pump and the switch.

* * * * *

UNITED STATES PATENT AND TRADEMARK OFFICE
CERTIFICATE OF CORRECTION

PATENT NO. : 6,482,640 B1  Page 1 of 1
DATED : November 19, 2002
INVENTOR(S) : Tanaka et al.

It is certified that error appears in the above-identified patent and that said Letters Patent is hereby corrected as shown below:

<u>Title page, Item [54] and Column 1, lines 1-2,</u>
Please delete "HYBRIDIZATION DEVICE, CASE, SUPPORT, AND LABEL AGENT" and replace it with -- HYBRIDIZATION DEVICE, CASE, SUPPORT, AND LABELING REAGENT --

Signed and Sealed this

Twenty-fifth Day of March, 2003

JAMES E. ROGAN
*Director of the United States Patent and Trademark Office*